United States Patent [19]
Watanabe et al.

[11] Patent Number: 5,621,009
[45] Date of Patent: Apr. 15, 1997

[54] CHONDROPROTECTIVE AGENTS

[75] Inventors: Koju Watanabe; Koichi Niimura, both of Saitama; Kiyonori Umekawa, Chiba, all of Japan

[73] Assignee: Kureha Chemical Industry Co., Ltd., Tokyo, Japan

[21] Appl. No.: 535,516

[22] Filed: Sep. 28, 1995

Related U.S. Application Data

[63] Continuation of Ser. No. 272,574, Jul. 11, 1994, abandoned.

[30] Foreign Application Priority Data

Jul. 9, 1993 [JP] Japan ................................ 5-194183

[51] Int. Cl.⁶ ........................................... A61K 31/19
[52] U.S. Cl. ................................. 514/568; 514/825
[58] Field of Search ................................. 514/568

[56] References Cited

FOREIGN PATENT DOCUMENTS 0083285  7/1983  European Pat. Off. .

OTHER PUBLICATIONS

Indian J. Exp. Biol., "Anti–Inflammatory Action of Ferulic Acid and Its Esters in Carrageenan Induced Rat Paw Oedema Model" by A.S. Chawla et al, vol. 25, No. 3, Mar. 1987, pp. 187–189.

Acta Zool. Sin., "Ultrastructural Observation on the Effects of Ferulic Acid on the Cartilage Proteoglycans in young Rats" by B.S. Zhou et al, vol. 38, No. 1, Mar. 1992, pp. 106–107.

Wuhan Daxue Xuebao, Ziran Kexueban, "Action of Derulic Acid and Sodium Selemite on Young Rats" by B.S. Zhou et al, No. 4, 1990, pp. 93–97.

Biotechnol. Ther., "Metabolic Activation of Phenols by Stimulated Neutrophils: A Concept for a Selective Type of Anti–Inflammatory Drug" by B.A. 'T Hart et al, vol. 3, No. 3–4, 1992, pp. 119–135.

Acupunct. Electro–Ther. Res. Int. J., "A Pharmacological Study of the Anti–Inflammatory Activity of Chinese Herbs. A Review." by J. Cyong et al, vol. 7, No. 2–3, 1982, pp. 173–202.

Clin. Chim. Act., "The Effect of Uraemic Metabolites on Parathyroid Extract–Induced Bone Resorption In Vitro" by M.R. Wills et al, vol. 73, No. 1, 1976, pp. 121–125.

*Primary Examiner*—Theodore J. Criares
*Attorney, Agent, or Firm*—Sughrue, Mion, Zinn, Macpeak & Seas

[57] ABSTRACT

A chondroprotective agent comprising a carboxylic acid compound of the general formula (I):

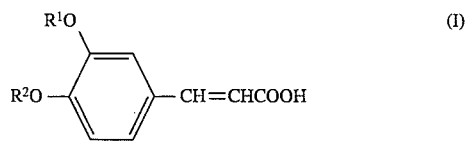

wherein $R^1$ and $R^2$ are, independently, a hydrogen atom or an alkyl group of 1 to 6 carbon atoms, or a cis- or trans-isomer thereof, or a pharmaceutically acceptable salt or ester thereof, and a pharmaceutically acceptable carrier is disclosed. The above compound strongly inhibits proteoglycan depletion from the chondrocyte matrix and exhibits a function to protect cartilage, and thus, is extremely effective for the treatment of arthropathy.

3 Claims, No Drawings

CHONDROPROTECTIVE AGENTS

This is a continuation of application Ser. No. 08/272,574, filed Jul. 11, 1994, now abandoned.

BACKGROUND OF THE INVENTION

1. Field of the Invention

The present invention relates to an agent for protecting cartilage, i.e., a chondroprotective agent, more particularly, a chondroprotective agent containing a carboxylic acid compound of the general formula (I) as mentioned below or a cis- or trans-isomer thereof, or a pharmaceutically acceptable salt or ester thereof.

2. Description of the Related Art

There are various types of arthropathy, for example, rheumatoid arthritis, rheumatic fever, and osteoarthritis. Many people particularly suffer from rhematoid arthritis and osteoarthritis. These diseases have been studied as the major types of arthropathy. There are congenital and secondary osteoarthritis, and further primary osteoarthritis caused by degeneration of the articular cartilage along with aging. Patients suffering from primary osteoarthritis have recently been increasing along with the increase in the population of the aged.

Although there are considerable differences of the causes and conditions between rheumatoid arthritis and osteoarthritis, the articular function becomes eventually obstructed by the destruction of the cartilage in both of rheumatoid arthritis and osteoarthritis.

The first choice of medicines for the treatment of rheumatic diseases such as rheumatoid arthritis, rheumatic fever, systemic lupus erythematosus, and osteoarthritis are analgesic and anti-inflammatory agents, for example, aspirin or indometacin. Further, gold compounds such as Shiosol, immunomodulators, steroids, or D-penicillamine are used as medicines for the treatment of rheumatoid arthritis.

The above conventional analgesic and anti-inflammatory agents, however, were not effective against the destruction of the articular cartilage, and in fact, sometimes exhibited adverse effects in experiments using chondrocytes. Further, no inhibitory effect on the destruction of articular cartilage was observed in the above medicines for the treatment of rheumatoid arthritis.

It is known that caffeic, ferulic, isoferulic, or 3-ethoxy-4-hydroxycinnamic acid may be used in the following pharmaceutical applications: Caffeic and ferulic acids exhibit an antiviral activity [Japanese Unexamined Patent Publication (Kokai) No. 4-234319]. Caffeic acid may be used as a calcium antagonist [Japanese Unexamined Patent Publication (Kokai) No. 4-243822], an anti-allergenic agent [Japanese Unexamined Patent Publication (Kokai) No. 59-155314], and the like. Caffeic acid and methyl caffeate can be used for the treatment of autoimmune disorders (WO91/17749). Further, ferulic and isoferulic acids may be used as an antitumor agent for preventing drug resistance in immunochemotherapy [Japanese Unexamined Patent Publication (Kokai) No. 56-115716]. Further, ferulic acid may be used as a composition for mitigating hyperlipemia and platelet aggregation (U.S. Pat. No. 4,842,859). Further, ferulic acid and esters thereof exhibit an anti-inflammatory action (A. S. Chawla et al., Indian J. Exp. Biol., Vol. 25, No. 3, pp. 187 to 189, 1987). 3-Ethoxy-4-hydroxycinnamic acid may be used as an ultraviolet absorbent for cosmetics [Japanese Unexamined Patent Publication (Kokai) No. 64-13018].

The above carboxylic acids, the cis- and trans-isomers thereof, the salts and the esters have not, however, been known to be useful as chondroprotective agents.

SUMMARY OF THE INVENTION

The present inventors engaged in intensive research to develop a chondroprotective agent for suppressing the destruction of the articular cartilage and as a result found that the particular carboxylic acid compounds, and cis- and trans-isomers thereof, and pharmaceutically acceptable salts, and esters thereof showed significant inhibition of the depletion of proteoglycan which is a major component of the cartilage matrix, and therefore, are useful as a chondroprotective agent for prohibiting the destruction of the articular cartilage.

Accordingly, the object of the present invention is to provide a chondroprotective agent containing as an active ingredient a particular carboxylic acid compound of the general formula (I), or a cis- or trans-isomer thereof, or a pharmaceutically acceptable salt or ester thereof.

Other objects and effects of the present invention will be clear from the following description.

The present invention relates to a chondroprotective agent comprising a carboxylic acid compound of the general formula (I):

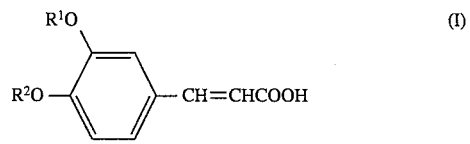

wherein $R^1$ and $R^2$ are, independently, a hydrogen atom or an alkyl group of 1 to 6 carbon atoms, or a cis- or trans-isomer thereof, or a pharmaceutically acceptable salt or ester thereof (hereinafter referred to as "the present substance").

DETAILED DESCRIPTION OF THE PREFERRED EMBODIMENTS

In the general formula (I), $R^1$ and $R^2$ are preferably a hydrogen atom or lower alkyl groups having 1 to 4 carbon atoms, more preferably methyl, ethyl, n-propyl, or n-butyl groups.

There exist a cis-form and a trans-form as to the configuration of the phenyl group and carbonyl group bonded at both sides of the double bond in the present substance. Each of the cis- and trans-forms may be used for the chondroprotective agent of the present invention.

As the pharmaceutically acceptable salts, there may be mentioned salts with alkali metals (such as sodium or potassium), salts with alkali earth metals (such as calcium or magnesium), aluminum salts, ammonium salts, salts with various amine compounds (such as primary, secondary, or tertiary amines), or the like.

The esters may be those with aromatic or aliphatic alcohols, preferably those with aliphatic alcohols, more preferably those with aliphatic alcohols having 1 to 6 carbon atoms. As even more preferable examples, there may be mentioned methyl, ethyl, n-propyl, isopropyl, n-butyl, isobutyl, t-butyl, n-pentyl, or isopentyl esters.

Examples of the present substance are listed in Table 1. Table 1 shows only the trans-forms, to which, however, the present invention is not limited.

TABLE 1

| R¹ | R² | Ester | Name | Abbreviation |
|----|----|-------|------|--------------|
| H  | H  |       | Caffeic acid | CFA |
| Me | H  |       | Ferulic acid | FLA |
| H  | Me |       | Isoferulic acid | IFLA |
| Et | H  |       | 3-Ethoxy-4-hydroxycinnamic acid | 3-EtO-4-HO-CA |
| Me | H  | (Na salt) | Sodium ferulate | NaFLA |
| Me | H  | Me | Methyl ferulate | MeFLA |
| Me | H  | Et | Ethyl ferulate | EtFLA |
| Me | H  | nPr | n-Propyl ferulate | nPrFLA |
| Me | H  | nBu | n-Butyl ferulate | nBuFLA |

Me: methyl, Et: ethyl, nPr: n-propyl, nBu: n-butyl

Many carboxylic acid compounds described in Table 1 are commercially available. For example, caffeic acid is available from Tokyo Kasei Kogyo Co. and ferulic and isoferulic acids is available from Sigma Chemical Co. Further, 3-ethoxy-4-hydroxycinnamic acid may be prepared by reacting 3-ethoxy-4-hydroxybenzaldehyde and malonic acid in the presence of a base such as pyridine (see Example 1 as below).

The pharmaceutically acceptable salts of the free carboxylic acids of the general formula (I) may be prepared by reacting hydroxides or carbonates of alkali metals, alkaline earth metals or ammonium, with an equimolar amount of said free carboxylic acids in a solvent such as water.

The ester of the free carboxylic acid of the general formula (I) may be prepared by reacting alcohol compounds with the above-mentioned free carboxylic acids in one of the following methods comprising:

(1) reacting an alcohol compound and the carboxylic acid in a suitable solvent in the presence of an acid catalyst, for example, an inorganic acid, such as hydrochloric, sulfuric or phosphoric acid, or an organic acid, such as acetic or p-toluene sulfonic acid;

(2) reacting an alcohol compound and the carboxylic acid in the presence of a condensation agent, such as dicyclohexylcarbodiimide, N,N'-carbonyldi(2-methylimidazole), diphenylketene-N-cyclohexylimine, alkoxyacetylene, ethyl polyphosphate, thionyl chloride, or oxalyl chloride, in an organic solvent, such as dimethylformamide, acetone, dioxane, acetonitrile, chloroform, ethylene chloride, tetrahydrofuran, or pyridine, generally with cooling or at room temperature;

(3) reacting a carboxylic acid anhydride and an alcohol compound in the presence of a basic material, such as triethylamine, pyridine, or methylethylpyridine; or (4) reacting a carboxylic acid halide, for example, acyl halide, such as chlorides or bromides, and an alcohol compound in a solvent containing a basic substance, such as triethylamine, pyridine or methylethylpyridine, or in a basic solvent, such as pyridine.

As clear from the toxicity shown below, the present substance is an extremely safe compound.

(1) Acute toxicity of caffeic acid

The LDLO (minimum lethal dose) for intraperitoneal administration in rats is 1500 mg/kg (Toxicology and Applied Pharmacology, Vol. 36, p. 227, 1976).

(2) Acute toxicity of ferulic, isoferulic, and 3-ethoxy-4hydroxycinnamic acids

Each of the above acids was orally administered at the dose of 400 mg/kg to ddY male mice (five mice per group) and the mice were observed for 1 week after the administration. The substances to be tested were orally administered after dispersed in an aqueous solution of 0.3% CMC (carboxymethylcellulose) and 0.05% Tween 80 (polyoxylethylene sorbitan monooleate; Tokyo Kasei Kogyo Co.), No deaths or no abnormalities in the body weight or general condition were observed in each of the substances to be tested.

The same results were obtained where sodium ferulate, methyl ferulate, ethyl ferulate, propyl ferulate, or butyl ferulate was administered.

The $Lb_{50}$ values of methyl ferulate and isopropyl ferulate in intraperitoneal administration to mice are 1188.5 mg/kg and 1059.2 mg/kg, respectively (A. S. Chawla et al., Indian J. Exp. Biol., Vol. 25, No. 3, pp. 187 to 189, 1987).

As a pharmacological effect, the present substance exhibits the function to inhibit destruction of chondrocyte matrix in cultured chondrocytes (derived from cartilage of rabbit shoulder and knee joints) (see Example 2 as below). Although the ester compound of the present invention does not always exhibit such a pharmacological effect in vitro, the function to inhibit cartilage destruction induced by granuloma was observed in animal experiments of a mouse air pouch model.

Accordingly, the present substance is useful as a chondroprotective agent for treating various types of arthropathy accompanying the cartilage destruction of joints. Examples of such arthropathy are rheumatoid arthritis, osteoarthritis, periarthritis humeroscapularis, shoulder-arm-neck syndrome, lumbago, etc.

The chondroprotective agent containing the present substance as an active ingredient may be in the form of any conventional formulation. The chondroprotective agent may contain the present substance alone, or a mixture of the present substance with any pharmaceutically acceptable carrier or diluent. The chondroprotective agent may contain the active ingredient in an amount of 0.01 to 100 percent by weight, preferably 0.1 to 70 percent by weight.

The chondroprotective agent of the present invention may be administered orally or by some other routes.

The dose of the chondroprotective agent according to the present invention varies with the patient (animal or human), age, individual differences, state of illness, and the like. Generally speaking, however, when a human is treated, the dose of oral administration of the present substance is in the range of 0.1 to 500 mg/kg (body weight) per day, preferably 0.5 to 200 mg/kg (body weight), which is usually divided into 1 to 4 dosages in a day, although the dose outside the above range may sometimes be administered.

EXAMPLE

The present invention now will be further illustrated by, but is by no means limited to, the following Examples.

Example 1: Preparation of Present Substance (1) Preparation of 3-ethoxy-4-hydroxycinnamic acid Malonic acid (1.56 g) and pyridine (3.0 ml) were placed in an egg-plant type flask (100 ml). Further, 3-ethoxy-4-hydroxybenzaldehyde (1.66 g) and aniline (30 µl) were added thereto and a reaction was performed at 55° C. for 3 hours. The reaction solution was acidified by adding dilute sulfuric acid. The crude crystals were obtained by filtration, washed with water, and then dried to obtain the above-identified compound (1.1 g, 56.1%) as a light yellowish crystal. Melting point: 157°–158° C.

$^1$H-NMR (CDCl$_3$, δ ppm): 1.40 (t, 3H, J=6.87 Hz, CH$_3$), 4.19 (q, 2H, J=6.87 Hz, CH$_2$), 6.36 (d, 1H, J=16.04 Hz), 6.87 (d, 1H, J=8.2 Hz), 7.13 (dd, 1H, J=8.2, 1.8 Hz), 7.31 (s, 1H), 7.59 (d, 1H, J=16.04 Hz)

IR spectrum (cm$^{-1}$): 3550s, 2980s, 2900s, 2830s, 2700m, 2600m, 2550m, 2510m, 1675s, 1625s, 1590s, 1515s, 1482m, 1435m, 1415m, 1330m, 1290s, 1260s, 1235s, 1195s, 1165s, 1121s, 1035s (2) Preparation of methyl ferulate Ferulic acid (4.85 g) and then methyl alcohol (50 ml) containing hydrogen chloride (4%) were placed in an eggplant type flask (200 ml), and heated under reflux for 1 hour. The disappearance of the starting material was confirmed by thin layer chromatography (TLC: n-hexane/ethyl acetate=2/1), then the solvent was evaporated under reduced pressure by a rotary evaporator. Benzene was added to the residue, and then, the solvent was again evaporated by a rotary evaporator to obtain the crude product. The resulting crude product was separated and purified by silica gel column chromatography (diameter=5.5×7.0 cm; 60 g; n-hexane/ethyl acetate=2/1) to obtain the above-identified compound. The product was crystallized from n-hexane to obtain a white crystal (5.09 g; 97.9%).

Melting point: 63°–64° C.

$^{1}$H-NMR (CDCl$_3$, δ ppm): 3.79 (s, 3H, COOCH$_3$), 3.90 (s, 3H, OCH$_3$), 6.08 (s, 1H, OH), 6.28 (d, 1H, J=15.6 Hz, H3), 6.91 (d, 1H, J=8.25 Hz), 7.01 (d, 1H, J=1.74 Hz), 7.04 (dd, 1H, J=8.25, 1.74 Hz), 7.62 (d, 1H, J=15.6 Hz, H4)

(3) Preparation of ethyl ferulate

Ferulic acid (4.85 g) and then ethyl alcohol (50 ml) containing hydrogen chloride (4%) were placed in an eggplant type flask (200 ml), and heated under reflux for 2.5 hours. The disappearance of the starting material was confirmed by TLC (n-hexane/ethyl acetate=2/1), then the solvent was evaporated under reduced pressure by a rotary evaporator. Benzene was added to the residue, and then, the solvent was again evaporated by a rotary evaporator to obtain the wine-colored crude product (5.79 g). The resulting crude product was separated and purified by silica gel column chromatography (diameter=5.5×7.0 cm; 60 g; n-hexane/ethyl acetate=3/1) to obtain the above-identified compound (5.06 g; 91.2%). The product was crystallized from n-hexane to obtain a white crystal (4.743 g, 85.3%).

Melting point: 41°–43° C.

$^{1}$H-NMR (CDCl$_3$, δ ppm): 1.33 (t, 3H, COOCH$_2$CH$_3$), 3.91 (s, 3H OCH$_3$), 4.25 (q, 2H, J=7.33 Hz), 6.06 (s, 1H, OH), 6.28 (d, 1H, J=15.6 Hz), 6.91 (d, 1H, J=6.8 Hz), 7.02 (s, 1H), 7.06 (d, 1H, J=8.25 Hz), 7.61 (d, 1H, J=15.6 Hz)

(4) Preparation of n-propyl ferulate

Ferulic acid (4.85 g) and then n-propyl alcohol (50 ml) containing hydrogen chloride (4%) were placed in an eggplant type flask (200 ml), and heated under reflux overnight. The disappearance of the starting material was confirmed by thin layer chromatography (TLC: n-hexane/ethyl acetate=2/1), then the solvent was evaporated under reduced pressure by a rotary evaporator. Benzene was added to the residue, and then, the solvent was again evaporated by a rotary evaporator to obtain the crude product. The resulting crude product was separated and purified by silica gel column chromatography (diameter=5.5×7.0 cm; 60 g; n-hexane/ethyl acetate=2/1) to obtain the above-identified compound (5.48 g, 91.6%) as colorless oil.

$^{1}$H-NMR (CDCl$_3$, δ ppm): 0.99 (t, 3H, J=7.33 Hz), 1.72 (s, 2H, J=7.33 Hz), 3.90 (s, 3H, OCH$_3$), 4.16 (t, 2H, J=6.9 Hz), 6.11 (s, 1H, OH), 6.30 (d, 1H, J=15.6 Hz), 6.91 (d, 1H, J=8.25 Hz), 7.02 (s, 1H), 7.05 (dd, 1H, J=8.23 Hz), 7.61 (d, 1H, J=15.6 Hz)

(5) Preparation of n-butyl ferulate

Ferulic acid (5 g) and then n-butyl alcohol (50 ml) containing hydrogen chloride (4%) were placed in an eggplant type flask (200 ml), and heated under reflux for about 2 hours. The disappearance of the starting material was confirmed by thin layer chromatography (TLC: n-hexane/ethyl acetate=2/1), then the solvent was evaporated under reduced pressure by a rotary evaporator. Benzene was added to the residue, and then, the solvent was again evaporated by a rotary evaporator to obtain the crude product. The resulting crude product was separated and purified by silica gel column chromatography (diameter=5.5×8.5 cm; 70 g; n-hexane/ethyl acetate=2/1) to obtain the above-identified compound (6.25 g, 99%) as colorless oil.

$^{1}$H-NMR (CDCl$_3$, δ ppm): 0.96 (t, 3H, J=7.33 Hz), 1.44 (seq, 2H J=7.33 Hz), 1.68 (quint, 2H, J=6.88 Hz), 3.91 (s, 3H), 4.21 (t, 2H, J=6.88 Hz), 6.04 (s, 1H, OH), 6.29 (d, J=16.0 Hz, 1H), 6.91 (d, J=8.25 Hz), 7.02 (s, 1H), 7.05 (dd, J=8.25 Hz)

Example 2: Effect of Test Compounds on Proteoglycan Depletion in Chondrocyte Culture (a) Preparation of Cultured Chondrocytes The cartilages were sterilely extracted from the shoulder and knee joints of rabbits (New Zealand White Rabbits) (body weight of 1 to 1.5 kg). The cartilages were thoroughly washed with phosphate buffer (PBS (−): free of Ca$^{2+}$, Mg$^{2+}$), Hanks' solution and 0.1% EDTA-PBS (−), and then cut into small segments (1 mm×1 mm×1 mm). After PBS (−) containing 0.1% EDTA was added, the segments were allowed to stand in an incubator of 37° C. for 30 minutes. Then, the segments were treated with a trypsin solution (0.25%) at 37° C. for one hour to remove the connective tissue adhered to the cartilage. After the supernatant had been removed, the cartilages were treated for about 2 to 2.5 hours in a Ham F-12 medium containing 10% fetal bovine serum (FBS) and 0.2% collagenase. Then, the collagenase solution was centrifuged (1500 r.p.m.), and the residual chondrocytes were washed twice with a Ham F-12 medium (chondrocyte culture medium) containing 10% FBS. Finally, the resulting suspension was adjusted so that the chondrocytes were suspended in the concentration of 3×10$^5$ cells/ml in the chondrocyte culture medium. The chondrocytes were seeded in an amount of 1 ml/well on 24-well plates. The chondrocytes became confluent 4 days later. The experiment were performed within two weeks after reaching the confluent stage.

(b) Addition of Compounds to be Tested and Proteoglycan Depleting Agents

The chondrocyte culture medium which had been used for cultivating the chondrocytes was removed from each well and 800 μl of fresh serum-free S-Clone medium containing 0.1% human serum albumin was added. Further, 100 μl of S-Clone medium containing the compounds to be tested (containing the compound in the concentration of 10 fold the final concentration; DMSO concentration=2.5%) was added. The chondrocytes were cultured in the presence of carbon dioxide (5%) and air (95%) for 2 hours. Then, the proteoglycan depleting agent, PMA (phorbol myristate acetate) (final concentration=0.1 μg/ml) or interleukin-1α (IL-1α) (final concentration=20 μ/ml) was added into the culture medium of the chondrocytes.

The compounds to be tested were as follows:

Compounds of present invention: caffeic acid (CFA: Tokyo Kasei Kogyo Co., Ltd.), ferulic acid (FLA: Sigma Chemical Co.), and 3-ethoxy-4-hydroxycinnamic acid (3-EtO-4-HO-CA: compound prepared by Example 1(1))

Comparative substance: Indometacin (Sigma Chemical Co.)

(c) Determination of proteoglycan

Proteoglycan depletion was determined by the measurement of the glycosaminoglycan (major constituent of proteoglycan, hereinafter referred to as GAG) content following digestion of the chondrocyte matrix with papain.

After 2 days, the supernatant of the chondrocyte culture was removed. Then, 1 ml of 0.03& papaine solution was added to the remaining chondrocyte matrix layer and a reaction was performed at 65° C. for 1 hour to liberate the GAG from the matrix layer. The content of the GAG in the treated papaine solution was determined by the 1,9-dimethylmethylene blue method (refer to R. W. Farndale, Biochim. Biophys. Acta., Vol. 883, pp. 173 to 177, 1986). The GAG content in the chondrocyte matrix of the control test wherein the proteoglycan depleting agent was not added was shown as "100", and the relative amount of the GAG of each experiment except the control test was calculated by by following formula:

GAG relative amount (%)=(B/A)×100 wherein A represents the GAG content of the control tests wherein the proteoglycan depleting agent was not added, and B represents the GAG content wherein the proteoglycan depleting agents were added alone or the GAG content wherein the proteoglycan depleting agents and the compounds to be tested were added.

The GAG contents of the control tests varied in a range of 28.0 to 74.5 μg/ml, depending on the period from the time when the chondrocytes became confluent until the time when the chondrocytes were used in the above experiment.

The results are shown in Table 2. The GAG content is the value of the mean value ± standard error (n=3). For each of the compounds to be tested, the control test and the proteoglycan depleting test wherein the proteoglycan depleting agent was added were carried out and the results thereof are also shown. The significance was determined by Student's t-test with respect to the proteoglycan depleting test wherein the proteoglycan depleting agent was added. The results of the determination are shown as follows:

*: $P<0.05$;
**: $P<0.01$;
***: $P<0.001$.

In comparison with the GAG content in the control tests wherein the proteoglycan depleting agent was not added, the addition of the proteoglycan depleting agents, PMA or IL-Iα, induced a loss of GAG content. Under these conditions, the present compound significantly inhibited or reduced the loss of GAG content, and showed a function to inhibit or suppress the proteoglycan depletion. On the contrary, indomethacin, a conventional analgesic and anti-inflammatory agent, did not show the function to inhibit or suppress the proteoglycan depletion, but showed a significant exacerbation on the cartilage destruction.

TABLE 2

| Samples | GAG content (μg/ml) | (Relative amount of GAG) (%) |
|---|---|---|
| Control | 43.2 ± 1.5** | (100) |
| IL-1α | 33.4 ± 1.0 | (77.3) |
| IL-1α + FLA (100 μM) | 39.9 ± 0.8** | (92.4) |
| IL-1α + CFA (100 μM) | 40.9 ± 0.7*** | (94.7) |
| Control | 43.4 ± 1.7** | (100) |

TABLE 2-continued

| Samples | GAG content (μg/ml) | (Relative amount of GAG) (%) |
|---|---|---|
| PMA | 32.1 ± 1.6 | (74.0) |
| PMA + FLA (100 μM) | 41.1 ± 4.2 | (94.7) |
| PMA + CFA (100 μM) | 47.7 ± 1.5*** | (110) |
| Control | 74.5 ± 0.6** | (100) |
| PMA | 46.2 ± 0.8 | (62.0) |
| PMA + 3-EtO-4-HO—CA (100 μM) | 61.5 ± 0.4*** | (82.6) |
| Control | 28.0 ± 0.7*** | (100) |
| PMA | 15.4 ± 0.5 | (55.0) |
| PMA + indometacin | | |
| (10 μM) | 13.2 ± 0,6* | (47.1) |
| (33 μM) | 11.7 ± 0.8** | (41.8) |

Example 3: Effect of Test Compounds on Proteoglycan Depletion in Mouse Air Pouch Model The procedure used in the present Example was based on the method described in K. M. K. Bottomley et al., Br. J. Pharmacol., Vol. 93, pp. 627–635 (1988).

The femoral head cartilage (FHC; 40 to 50 mg) was sterilely taken out from S.D. rats (5.5 weeks old, female), wrapped in a cotton fabric (5 mm×5 mm; about 3 mg), and then, implanted subcutaneously in the backs (where 5 ml of air had been injected the day before) of BALB/c mice (7 weeks old, female).

n-Propyl ferulate [nPrFLA; prepared by Example 1(4)] dispersed in an aqueous solution of a mixture of CMC and Tween 80 (final concentration: CMC=0.3%, Tween 80=0.05%) was orally administered at the dose of 100 mg/kg, starting from the third day after implantation, at a rate of five times a week. An aqueous solution of a mixture of the CMC and Tween 80 was orally administered to the control group.

The implanted FHC's were taken out on the 21st day after implantation, and the FHC matrices were digested with a papain solution (4 u/ml papain, 0.05M PBS, pH 6.5, 10 ml). After digestion, the GAG content in the papain solution was determined by the 1,9-dimethyl methylene blue method (R. W. Farndale, vide supra).

In the case of the non-treated group, the FHC's were taken out on the third day after implantation and the GAG content was measured.

The results are shown in Table 3. The GAG content/FHC in the Table 3 is the value of the mean value±standard error (n=8 to 10) of the GAG content per FHC. The GAG relative amount (%) is the relative amount when the GAG content/FHC of the non-treated group is 100.

Cartilage destructive factor was secreted from the newly formed granuloma around the implanted FHC's. Therefore, a reduction of GAG was observed in the control group. On the contrary, suppression of the GAG reduction was observed in the group to which the present substance was administered and therefore the action of the present substance in suppressing cartilage destruction was confirmed.

Further, methyl ferulate, ethyl ferulate, and n-butyl ferulate exhibited effects similar to that of n-propyl ferulate.

TABLE 3

| Treatment | GAG content/FHC μg/FHC | Relative amount of GAG (%) |
| --- | --- | --- |
| No treatment | 745.8 ± 24.5 | (100) |
| Control | 387.1 ± 17.1 | (51.9) |
| nPrFLA | 435.3 ± 26.4 | (58.4) |

Example 4: Formulation of Granule

The following ingredients were mixed homogeneously:

| Ferulic acid | 20 parts by weight |
| --- | --- |
| Lactose | 68 parts by weight |
| Low-substituted hydroxypropylcellulose | 10 parts by weight |
| Hydroxypropylcellulose | 2 parts by weight |

The mixture was kneaded using 32 parts by weight of a wetting agent, ethanol. Then, the kneaded mixture was glanulated by wet granulation and dried to obtain the granule.

As explained above, the present substance strongly inhibits proteoglycan depletion from the chondrocyte matrix and exhibits a function to protect cartilage. Further, the present substance has low toxicity. Accordingly, the present substance is very useful for the treatment of arthropathy, such as rheumatoid arthritis, osteoarthritis, periarthritis humeroscapularis, shoulder-arm-neck syndrome, lumbago, and so on.

Although the present invention has been described with reference to specific embodiments, various changes and modifications obvious to those skilled in the art are deemed to be within the spirit, scope, and concept of the invention.

We claim:

1. A method for treating arthropathy accompanying the cartilage destruction of a joint, comprising the step of:

administering an effective amount of a chondroprotective agent to a mammal in need of said chondroprotective agent, wherein said chondroprotective agent comprises a carboxylic acid compound of general formula (I):

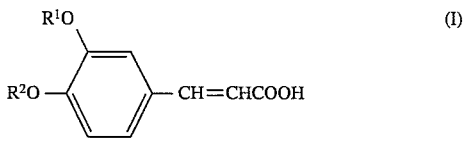

wherein $R^1$ and $R^2$ are, independently, a hydrogen atom or an alkyl group of 1 to 6 carbon atoms, or a cis- or trans-isomer thereof, or a pharmaceutically acceptable salt or ester thereof, with the proviso that when $R^1$ is a methyl group and $R^2$ is a hydrogen atom, the carboxylic acid is a cis-isomer, and a pharmaceutically acceptable carrier.

2. A method for treating arthropathy according to claim 1, wherein said pharmaceutically acceptable ester is an ester with an aliphatic alcohol having 1 to 6 carbon atoms.

3. A method for treating arthropathy according to claim 1, wherein the carboxylic acid compound of general formula (I) is at least one compound selected from the group consisting of caffeic acid, isoferulic acid, and 3-ethoxy-4-hydroxycinnamic acid.

* * * * *